(12) United States Patent
Hill

(10) Patent No.: US 10,485,961 B2
(45) Date of Patent: Nov. 26, 2019

(54) MEDICAL PROCEDURE FOR INSERTING A CHEST DRAINAGE TUBE

(71) Applicant: David A. Hill, Chicago, IL (US)

(72) Inventor: David A. Hill, Chicago, IL (US)

(*) Notice: Subject to any disclaimer, the term of this patent is extended or adjusted under 35 U.S.C. 154(b) by 218 days.

(21) Appl. No.: 15/641,001

(22) Filed: Jul. 3, 2017

(65) Prior Publication Data
US 2017/0296797 A1 Oct. 19, 2017

Related U.S. Application Data

(63) Continuation-in-part of application No. 13/870,275, filed on Apr. 25, 2013, now Pat. No. 9,694,164.

(51) Int. Cl.
*A61B 17/34* (2006.01)
*A61M 27/00* (2006.01)
*A61B 17/28* (2006.01)

(52) U.S. Cl.
CPC .......... *A61M 27/00* (2013.01); *A61B 17/282* (2013.01); *A61B 17/2841* (2013.01); *A61B 17/3415* (2013.01); *A61M 2210/101* (2013.01)

(58) Field of Classification Search
CPC . A61B 17/28; A61B 17/2812; A61B 17/2841; A61B 17/282; A61B 17/3201; A61B 17/3415; A61B 17/3417; A61B 17/3468; A61M 27/00; A61M 27/002; A61M 2027/004
See application file for complete search history.

(56) References Cited

U.S. PATENT DOCUMENTS

| | | | | |
|---|---|---|---|---|
| 4,608,982 A | * | 9/1986 | Pollard | A61B 17/2812 128/207.29 |
| 4,617,929 A | * | 10/1986 | Gill | A61M 25/06 128/207.29 |
| 4,889,112 A | * | 12/1989 | Schachner | A61B 17/2812 128/200.26 |

* cited by examiner

*Primary Examiner* — Ryan J. Severson
*Assistant Examiner* — Christian D Knauss
(74) *Attorney, Agent, or Firm* — Bycer Law, PLC; Matthew L. Bycer

(57) ABSTRACT

A single stage instrument is used to insert a chest drainage tube into the inter-pleural space to facilitate drainage. The instrument is scissor-like with cylinder-like channels to slidably enclose the distal section of the tube therein when closed. The tip of the instrument is curved to enter the skin incision and the offset pleural incision whereafter the instrument is rotated 180 degrees to align the curved tip with the pleural space. The curved tip facilitates sliding the chest drainage tube through the instrument to effect sufficient insertion length. Once the instrument is in place, the tube is slid along the instrument to ensure that all drainage holes in the chest drainage tube are within the pleural cavity. Thereafter, the instrument is withdrawn leaving the chest drainage tube in place. After withdrawal of the instrument, it is opened laterally for lateral disengagement with the chest drainage tube.

17 Claims, 3 Drawing Sheets

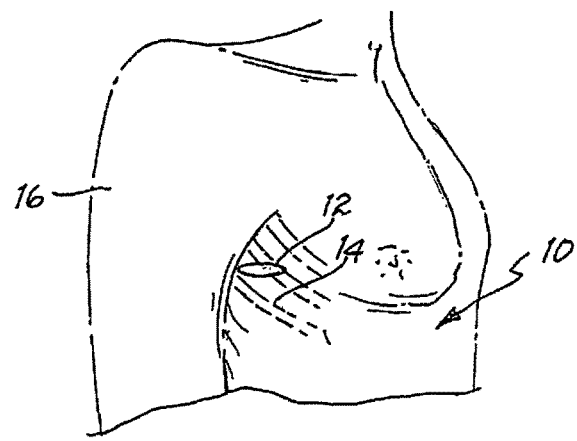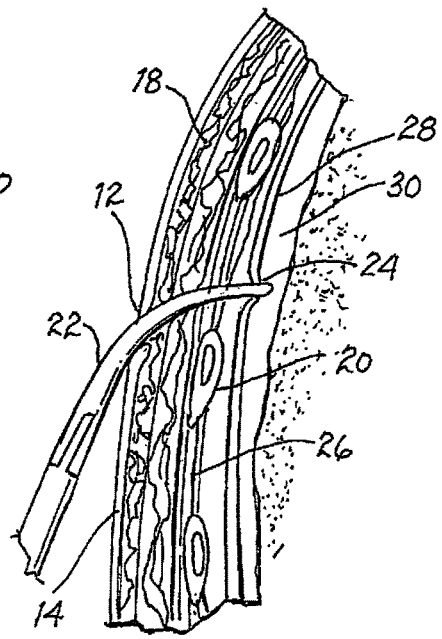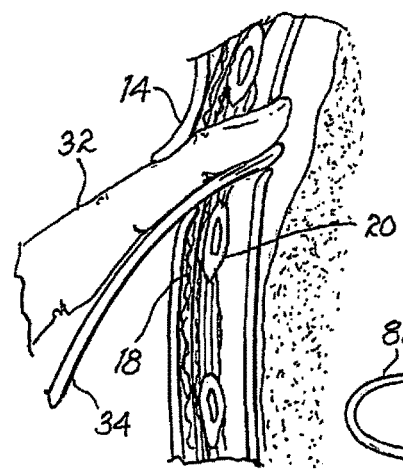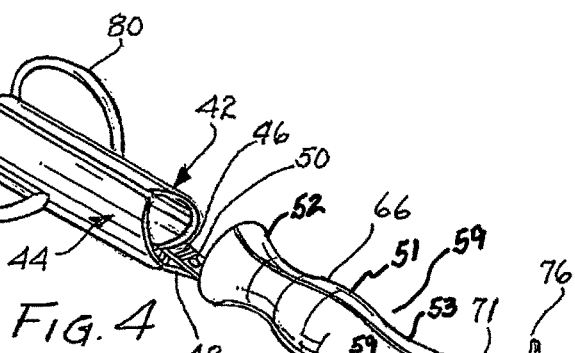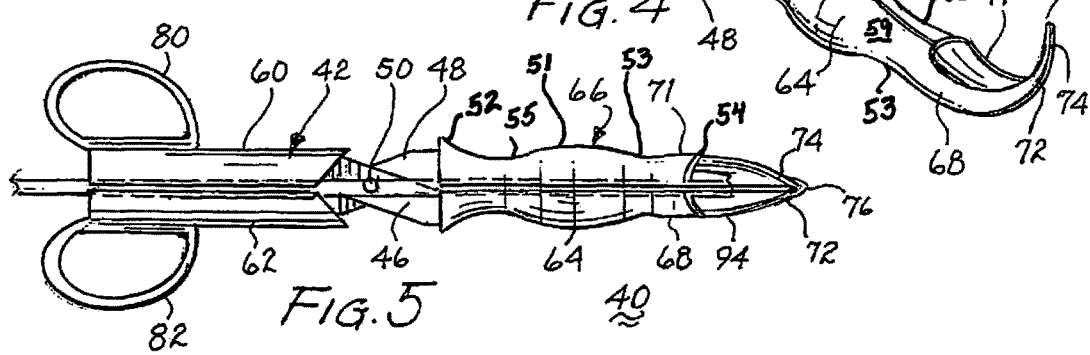

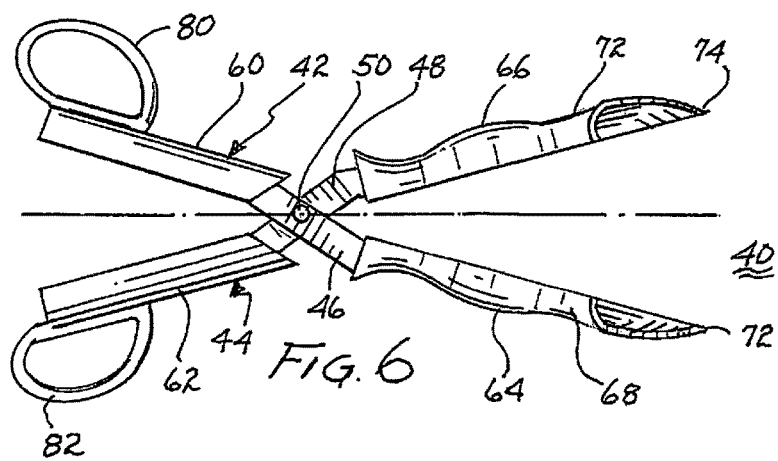
FIG. 6
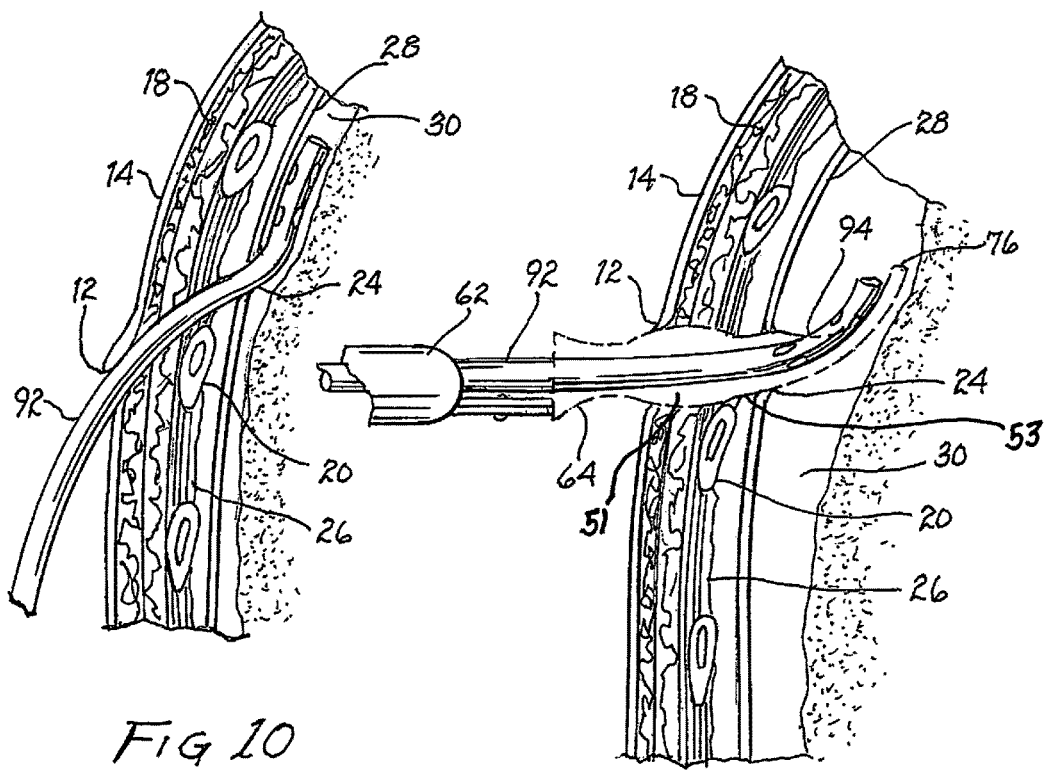
FIG 10
FIG. 9

MEDICAL PROCEDURE FOR INSERTING A CHEST DRAINAGE TUBE

BACKGROUND OF THE INVENTION

1. Field of the Invention

The present invention relates medical instruments and, more particularly, to an instrument for inserting a chest drainage tube and related method.

2. Description of Related Prior Art

Conventional chest drainage tubes typically include a plurality of apertures at the distal end for inflow of fluid within the parietal pleura and effect drainage. Heretofore, the insertion of the chest drainage tube has been primarily a manual function performed by the surgeon. This operation will be summarized below to emphasize the function and utility of the present invention.

An incision is made at the level of the fifth intercostal space overlying the sixth rib. In men, this is about at the nipple line and in women it is at the level of the xiphoid process or inframammary fold. The incision is made just anterior to the mid-axillary line in a horizontal fashion.

Betadine or chlorhexidine is used as the topical antibacterial/disinfectant prior to the procedure. The chest wall is widely prepped to ensure sterility. The patient's arm on the ipsilateral side (same side as placement of the drainage tube is placed) is elevated above the patient's head to allow for adequate access. The incision is made with a scalpel of approximately 3 cm in length after injection of local anesthetic into the skin, subcutaneous tissue, and just above the rib. Once this is done, dissection through subcutaneous tissue over the rib is done with a Kelly clamp. It is important to dissect the rib above the skin incision to offset the skin incision from the pleural incision so that when the chest drainage tube is pulled out eventually, the two openings do not line up. Further blunt dissection is carried out through the intercostals muscles with the clamp, during which time it is important to keep the clamp riding along the cephalad border of the rib so as to avoid damage to the intercostals vein, artery, and nerve. These structures are collectively known as the neurovascular bundle.

The parietal pleura is then carefully punctured with the clamp tip and the opening enlarged with a gloved finger. A 360 degree sweep is made to check the visceral pleura, lung surface, and any palpable adhesions. The chest drainage tube is then inserted with a clamp on the distal end, either with the aid of a finger or by following the path previously made. A second clamp may be placed on the proximal end (outside of the patient's body) if fluid is expected so as to prevent spillage. Once inserted through the parietal pleural opening, the distal clamp may be removed and the chest drainage tube advanced apically/cephalad. The chest drainage tube is inserted to at least 12 cm to ensure that all drainage holes on the tube are within the chest. For this reason, in very large patients the insertion may be 16 cm or more, and in smaller patients the insertion may need be only 10 cm.

The proximal clamp is then removed and the end of the chest drainage tube placed in a suction canister. The position of the chest drainage tube is verified by looking for tube condensation indicating good placement. Often times, the chest drainage tube is also rotated to confirm placement as it should turn freely if not kinked.

The chest drainage tube is sutured in place with the skin with a series of knots in silk suture and the end of the chest drainage tube placed to underwater seal or suction (−20 mm water), if not already done. A chest x-ray is taken to confirm proper position and function of the chest drainage tube. If needed, the chest drainage tube can be withdrawn if too far in the chest. It is never further advanced due to the risk of introducing skin contaminants into the chest.

Hemothorax (blood in the inter-pleural space) will often drain without wall suction (blood is forced out with respirations as the lung expands). Pneumothorax (air in the inter-pleural space) requires suction until no air leak remains.

SUMMARY OF THE INVENTION

The conventional procedure for inserting a chest drainage tube into the pleural cavity requires significant manual dexterity for the surgeon to use his/her finger and a clamp to manipulate the chest drainage tube into place. This procedure may be more or less time-consuming depending upon innumerable factors. By using the instrument described herein, the insertion of the chest drainage tube is primarily a mechanical function easily and rapidly performed. The instrument circumscribes the chest drainage tube during insertion and includes a tip for penetration after insertion through the initial incision. A ramp at the distal end of the chest drainage tube causes the chest drainage tube to bend into alignment with the pleural cavity upon sliding movement of the chest drainage tube through the instrument. After placement of the chest drainage tube, the instrument is withdrawn and opened to accommodate lateral withdrawal of the chest drainage tube from within the instrument. Subsequently, the chest drainage tube may be sutured in place.

It is therefore a primary object of the present invention to provide an instrument for mechanically inserting a chest drainage tube into the pleural cavity.

Another object of the present invention is to provide an instrument for bending a chest drainage tube during insertion of the chest drainage tube into alignment with the pleural cavity.

Still another object of the present invention is to provide an instrument that is openable to accommodate lateral insertion of a chest drainage tube and closeable to permit sliding movement of the chest drainage tube therethrough.

Yet another object of the present invention is to provide an instrument slidable along a chest drainage tube after insertion and openable to accommodate lateral withdrawal of the chest drainage tube from therewithin.

A further object of the present invention is to provide an instrument having finger grips for manipulating the instrument during insertion of a chest drainage tube and withdrawal of the instrument.

A still further object of the present invention is to provide a method for using an instrument to insert a chest drainage tube within the pleural cavity.

A yet further object of the present invention is to provide a method for reducing the level of manual skills required to insert a chest drainage tube into the pleural cavity.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates the incision to be made in the torso of a patient;

FIG. 2 illustrates the use of a surgeon's finger to assist in inserting a chest drainage tube into the pleural cavity;

FIG. 3 illustrates the use of a clamp to perform a conventional procedure for inserting a chest drainage tube into the pleural cavity;

FIG. 4 is an isometric view of an instrument for inserting a chest drainage tube into the pleural cavity;

FIG. 5 is a top view of the instrument in the closed position;

FIG. 6 is a top view of the instrument in the open position during insertion and withdrawal of a chest drainage tube;

FIG. 9 illustrates the process of using the instrument to slidably insert the chest drainage tube; and FIG. 10 illustrates the inserted chest drainage tube after withdrawal of the instrument.

DESCRIPTION OF THE PREFERRED EMBODIMENT

Figure 7:
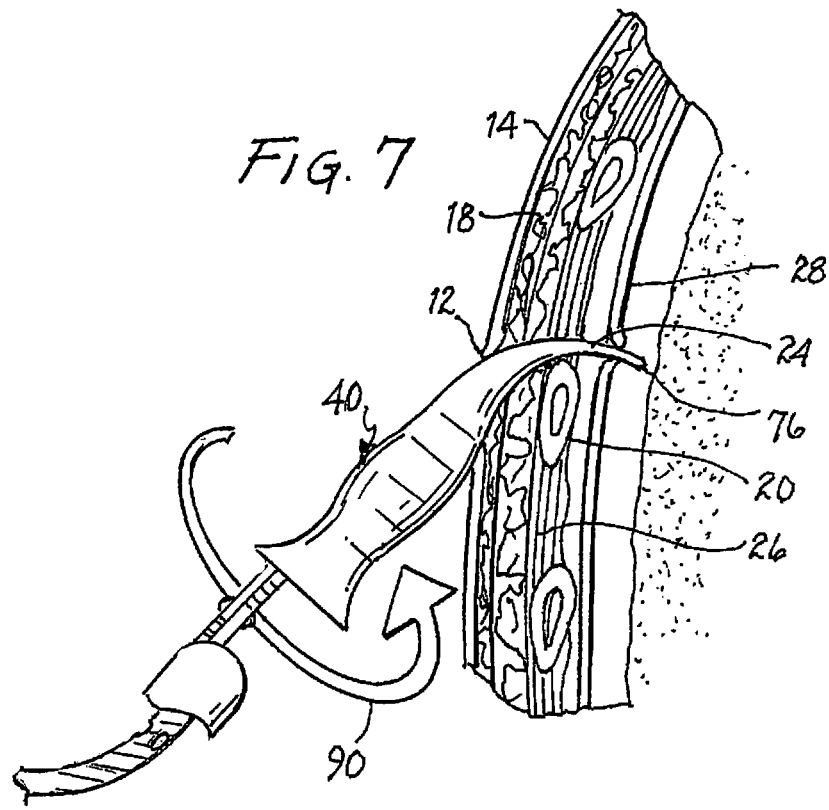
FIG. 7 illustrates insertion of the tip of the instrument followed by 180 degree rotation of the instrument.

Referring to FIGS. 1 and 2, there is shown a torso 10 of a man prior to insertion of a chest drainage tube in the pleural cavity. An incision 12 is made through skin 14 at the level of the fifth intercostal space overlying the sixth rib. The incision is made just anterior of the mid-axillary line in a horizontal fashion. The patient's arm 16 is elevated above the patient's head to allow for adequate access. The incision is 3 cm in length after injection of local anesthetic into skin 14, subcutaneous tissue 18, and just above rib 20. Once this is done, dissection through subcutaneous tissue 18 over rib 20 is done with a Kelly clamp 22.

It is important to dissect the rib above incision 12 to offset this incision from the pleural incision 24 so that the two incisions do not line up when the chest drainage tube is pulled out. Further blunt dissection is carried out through intercostal muscles with clamp 22 and it is important to keep the clamp riding along the cephalad border of rib 20 to avoid damage to the intercostals vein, artery, and nerve. These structures are collectively referred to as the neurovascular bundle.

Parietal pleura 28 is punctured with the tip of clamp 22. As particularly shown in FIG. 3, incision 24 is enlarged with a gloved finger 32. The chest drainage tube 34 is then inserted with clamp 22 on the distal end either with the aid of a finger, as shown in FIG. 3, or by following the path previously made. Once chest drainage tube 34 is inserted through parietal pleura opening 24, the distal clamp may be removed and the chest drainage tube advanced apically/cephalad.

This complex procedure is carried out more simply and more conveniently with instrument 40 shown in FIG. 4. In describing the structure of this instrument, reference will also be made to the top view of the instrument in the closed position, as shown in FIG. 5, and the top view of the instrument in the open position, as shown in FIG. 6. Instrument 40 includes two essentially mirror image elements 42, 44 pivotally connected through lands 46, 48, respectively, with a pivot 50. Element 42 includes semi-circular channel 60 (first channel) extending proximally from land 46. Similarly, element 44 includes a semi-circular channel 62 (second channel) extending proximally from land 48. The longitudinal openings of these channels face one another when in the closed position, as shown in FIG. 5, to form a tube or cylindrical enclosure.

A further channel 64 (third channel) extends from land 46. This channel is also semi-cylindrical but including different radius along the channel to provide an undulating exterior surface. A further channel 66 (fourth channel) extends from land 48. This further channel is also semi-cylindrical and has varying radii to provide an undulating exterior surface, as illustrated. Upon closure of instrument 40, as depicted in FIG. 5, further channels 64 and 66 define an essentially circular passageway therebetween, such as a tube or cylinder. A portion of side 68 of further channel 64 is cut away toward end 72 and forms a lateral opening, as illustrated in FIG. 5. Additionally, the remaining portion of side 68 toward end 72 is bent upwardly, as depicted in FIG. 4. Side 71 of further channel 66 also includes a cutaway toward end 74 to form a lateral opening, as depicted in FIG. 5. As with end 72, end 74 is bent upwardly in mating configuration with end 72 to form tip 76, as depicted in FIG. 4. To assist in manipulating instrument 40, finger grips 80, 82 may be attached to channels 62, 64, respectively. By using these finger grips, instrument 40 may be opened and closed at will to perform the procedure.

Exterior surface 59 of further channels 64 and 66 forms along sides 68 and 71, respectively. Exterior surface 59 may be shaped with an undulating surface. Back flange 52 serves to protect channels 60 and 62 as well as pivot 50 from exposure to bodily fluids. Back flange 52 may also be useful to gauge the distance inserted and serve as a back stop to indicate depth. Preferably bulge 51 serves as a backstop. In such a case as bulge 51 serves as a backstop, a rib, or as understood in the art the rib including related tissues, may rest in narrow 53 between bulge 51 and extending surface 54. Narrow 53 may be shaped to correspond, or otherwise compliment the shape of the rib, as is known in the art. Alternatively, second narrow 55 may be used as a catch for the rib when the back flange 52 is used as a back stop.

Figure 8:
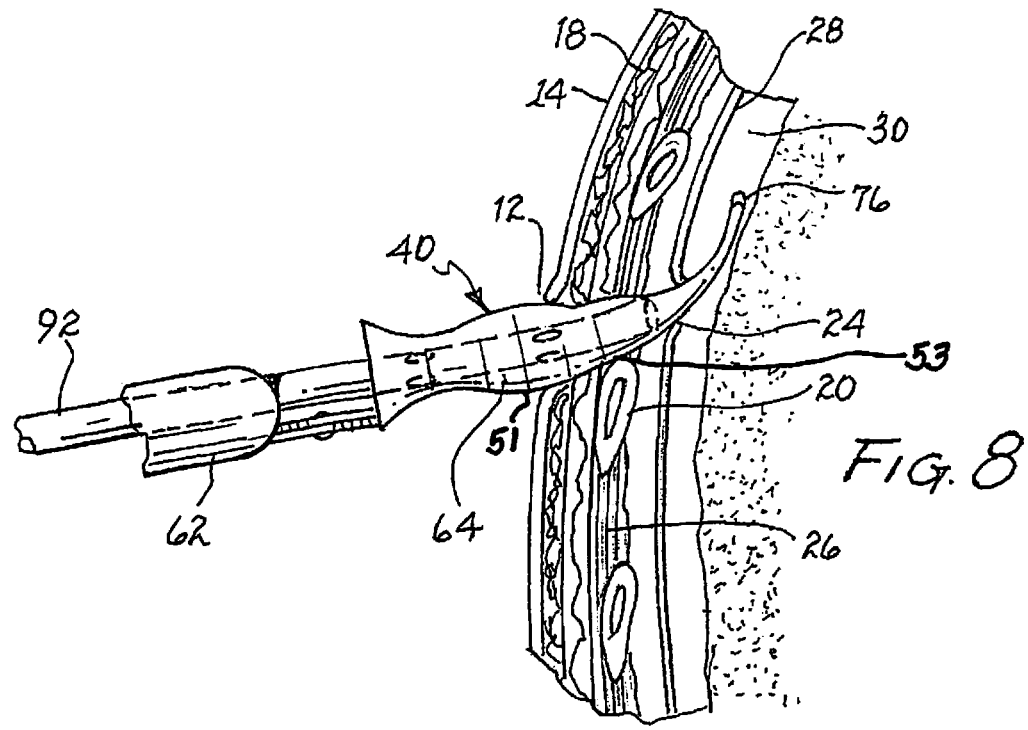
FIG. 8 illustrates the position of the instrument relative to the pleural cavity prior to insertion of the chest drainage tube.

Referring jointly to FIGS. 7, 8, 9 and 10, the above-described essentially manual procedures may be duplicated by use of instrument 40. Tip 76 of instrument 40 is inserted through incision 12 with further insertion as described above until pleural incision 24 is made. Preferably, the undulating shape of the tool is used to guide insertion. Insertion of the tool is made until the rib (as understood in the present invention, the term "rib" when used to describe the insertion of the tube refers to the rib and related tissues surrounding the rib, as well as the actual bone) rests into narrow 53, abutting bulge 51. Bulge 53 is preferably rounded whereby the diameter of the tool modulated from high and low areas to provide the undulating surface. Thereafter, instrument 40 is rotated approximately 180 degrees, as depicted by arrow 90. As a result, the orientation of further channels 64, 66 and tip 76 of instrument 40 will be as depicted in FIG. 8. Thereafter, chest discharge tube 92 is slid through channels 60, 62, of which only channel 62 is depicted, and further channels 64, 66, of which only channel 64 is depicted, in the side view shown in FIG. 8.

As chest discharge tube 92 is slid further through instrument 40, it becomes curved by the guidance provided by ends 72, 74 defining outlet aperture 94, as particularly shown in FIG. 9. Such bending of the chest discharge tube essentially aligns it with the pleural cavity after a sufficient length of the chest discharge tube has been slid into the pleural cavity.

As shown in FIG. 10, instrument 40 has been withdrawn by sliding it proximally along the chest discharge tube.

When clear of incision 12, instrument 40 is opened, as depicted in FIG. 6, and the instrument may be laterally moved to disengage it from the chest discharge tube. Suturing of the chest discharge tube and other medical procedures attendant the chest discharge tube may then be carried out without interference from instrument 40.

I claim:

1. A method for using an instrument having a pair of pivotally connected elements for inserting a chest drainage tube into the pleural space of a patient, said method comprising the steps of:
    (a) making a skin incision of an intercostal space overlying a rib;
    (b) inserting a curved tip of the instrument through subcutaneous tissue above the rib offset from the skin incision until the rib rests into a narrow region between a first distal ridge and a second proximal ridge along an exterior surface of the instrument;
    (c) puncturing a parietal pleura with the curved tip of the instrument and sliding the distal end of the instrument into the parietal pleura;
    (d) rotating the instrument to orient the curved tip into alignment with a pleural space after said step of puncturing and while the distal end is inserted into the parietal pleura;
    (e) moving the distal end of the instrument further into the parietal pleura;
    (f) sliding the chest drainage tube through the instrument past the curved tip to bend the chest drainage tube into alignment with the pleural space; and
    (g) withdrawing the instrument leaving the chest drainage tube in place.

2. The method as set forth in claim 1 wherein said step of withdrawing includes the step of opening the instrument to laterally release the chest drainage tube from therewithin.

3. The method as set forth in claim 1 wherein the two pivotally connected elements of the instrument define a passageway for the chest drainage tube when the instrument is in the closed position during said step of sliding and when the instrument is in the open position, longitudinally opening the passageway for accommodating said step of withdrawing.

4. The method as set forth in claim 3 wherein said step of withdrawing includes the step of opening the instrument to release the chest drainage tube from therewithin.

5. The method as set forth in claim 4 including the step of manually engaging a finger grip on each element to carry out said step of opening.

6. The method as set forth in claim 1 wherein said step of making a skin incision is made of the fifth intercostal space overlying the rib.

7. The method as set forth in claim 1 wherein said step of inserting further comprises the step of halting insertion when the rib reaches a back stop along the exterior surface of the instrument.

8. The method as set forth in claim 1 wherein the exterior surface of the instrument includes a portion shaped to complement the contour of a rib.

9. A method for inserting a chest drainage tube into the pleural space of a patient, said method comprising the steps of:
    (a) making a skin incision at the level of the fifth intercostal space overlying the sixth rib;
    (b) inserting a curved tip of an instrument through subcutaneous tissue above the sixth rib offset from the skin incision while avoiding the neurovascular bundle;
    (c) puncturing a parietal pleura with the curved tip of the instrument and sliding a distal end of the instrument into the parietal pleura;
    (d) rotating the instrument to orient the curved tip into alignment with the pleural space after said step of puncturing and while the distal end is inserted into the parietal pleura;
    (e) moving the distal end of the instrument further into the parietal pleura;
    (f) sliding the chest drainage tube through the instrument past the curved tip to bend the chest drainage tube into alignment with the pleural space; and
    (g) withdrawing the instrument leaving the chest drainage tube is in place.

10. The method of claim 9 wherein said step of rotating directs the curved tip towards a diaphragm so as to allow for fluid to drain from the pleural cavity.

11. The method of claim 9 wherein said step of rotating directs the curved tip upwards towards a neck to allow for gas to release from the pleural cavity.

12. The method of claim 9 wherein said step of inserting further comprises aligning a side edge of the instrument with a rib and sliding the instrument until the rib rests in a narrow beside a ridge of an exterior surface of the instrument.

13. The method of claim 12 wherein said step of inserting includes inserting the instrument with at least one undulating side.

14. The method of claim 13 wherein said step of inserting includes inserting the instrument with two generally half cylindrical shapes facing one another with the tube positioned therebetween, and each of the shapes exhibiting an undulating exterior surface including at least one ridge and at least one narrow.

15. The method of claim 14 wherein the undulating exterior surfaces of each of the shapes includes at least two ridges with a narrow positioned between the two ridges.

16. The method of claim 12 wherein the exterior surface of the instrument is shaped to compliment a contour of a rib.

17. The method of claim 9 wherein said step of inserting further comprises aligning a side edge of the instrument with a rib and sliding the instrument until the rib interacts with a back stop along an exterior surface of the instrument.

* * * * *